(12) United States Patent
Domb

(10) Patent No.: US 7,919,113 B2
(45) Date of Patent: Apr. 5, 2011

(54) DISPERSIBLE CONCENTRATE LIPOSPHERES FOR DELIVERY OF ACTIVE AGENTS

(75) Inventor: Abraham J. Domb, Efrat (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1078 days.

(21) Appl. No.: 10/965,551

(22) Filed: Oct. 14, 2004

(65) Prior Publication Data

US 2005/0158389 A1 Jul. 21, 2005

Related U.S. Application Data

(63) Continuation-in-part of application No. 09/869,519, filed as application No. PCT/IL99/00710 on Dec. 30, 1999.

(60) Provisional application No. 60/510,547, filed on Oct. 14, 2003.

(51) Int. Cl.
*A61K 9/127* (2006.01)
(52) U.S. Cl. ......... 424/450; 977/797; 977/799; 977/801
(58) Field of Classification Search .................. None
See application file for complete search history.

(56) References Cited

U.S. PATENT DOCUMENTS

| | | | |
|---|---|---|---|
| 5,342,625 A | 8/1994 | Hauer et al. | |
| 5,583,105 A | 12/1996 | Kovacs et al. | |
| 5,603,951 A | 2/1997 | Woo | |
| 5,614,491 A | 3/1997 | Walch et al. | |
| 5,639,474 A | 6/1997 | Woo | |
| 5,716,637 A * | 2/1998 | Anselem et al. | 424/450 |
| 5,741,512 A * | 4/1998 | Hauer et al. | 424/450 |
| 5,756,450 A | 5/1998 | Hahn et al. | |
| 5,798,333 A | 8/1998 | Sherman | |
| 5,827,822 A | 10/1998 | Floc'h et al. | |
| 6,004,580 A | 12/1999 | Backlund et al. | |
| 6,028,067 A | 2/2000 | Hong et al. | |
| 7,026,290 B1 * | 4/2006 | Domb | 514/11 |

FOREIGN PATENT DOCUMENTS

| | | |
|---|---|---|
| EP | 0760237 | 3/1997 |
| WO | WO 96/13273 | 5/1996 |
| WO | WO 97/04795 | 2/1997 |
| WO | WO 97/19692 | 6/1997 |
| WO | WO 98/33512 | 8/1998 |

OTHER PUBLICATIONS

The Merck Index, The Merck Index, 12th ed. Merck & Co. Inc. 1996.*

* cited by examiner

*Primary Examiner* — Carlos A Azpuru
(74) *Attorney, Agent, or Firm* — Pabst Patent Group LLP

(57) ABSTRACT

A formulation containing one or more lipophilic agents, methods of making and using the formulation are described herein. The formulation is formed by adding a pre-suspension concentrate composition to an aqueous medium. Upon contact with the aqueous medium, a solid nanoparticle suspension spontaneously forms. The resulting formulation is in the form of a microemulsion. The concentrate contains an amphiphilic solvent, a pharmaceutically acceptable solid carrier such as a solid fatty acid or ester, a surfactant, and an agent. Preferably the concentrate contains a combination of a surfactant with a high hydrophilic/lipophilic balance (HLB) of at least about 8 and a surfactant with a low HLB of less than about 5. The agent is preferably a lipophilic drug and other lipophilic ingredient, such as vitamins. The composition is suitable for use in medical and non-medical applications. The microemuslions described herein have increased stability was compared to the prior art.

18 Claims, No Drawings

DISPERSIBLE CONCENTRATE LIPOSPHERES FOR DELIVERY OF ACTIVE AGENTS

CROSS-REFERENCE TO RELATED APPLICATIONS

This application claims priority to provisional application Ser. No. 60/510,547, filed Oct. 14, 2003. This application is also a continuation-in-part of U.S. Ser. No. 09/869,519 filed Sep. 19, 2001, entitled "*Dispersible Concentrate for the Delivery of Cyclosporin*" by Abraham J. Domb, which is a §371 application of WO 00/40219, filed Dec. 30, 1999, which claims priority to U.S. Ser. No. 09/223,378, filed Dec. 30, 1998.

FIELD OF THE INVENTION

The present invention is generally in the field of dispersible concentrate preparations for the solubilization of lipophilic agents such as lipophilic drugs, and in particular, of a dispersible concentrate preparation which provides a delivery system with high bioavailability of water insoluble substances.

BACKGROUND OF THE INVENTION

The use of dispersion systems as carriers of biologically active compounds is well known in the art. These systems are designed to protect the biologically active compound from the environment during delivery and to provide a controlled release of the substance to a targeted area. In some cases, the goal is to target specific sites in the body using the dispersion. Alternatively, the drug carrier system acts as a reservoir at the site of injection.

Dispersion systems used for pharmaceutical and cosmetic formulations can be categorized as either suspensions or emulsions. Suspensions are defined as solid particles ranging in size from a few nanometers up to hundreds of microns dispersed in an aqueous or non-aqueous medium using suspending agents. Solid particles include microspheres, microcapsules, nanoparticles and nanospheres.

Emulsions are defined as dispersions of one liquid in another, stabilized by an interfacial film of emulsifiers such as surfactants and lipids. Despite their long history, emulsions are used less often today than other dosage forms due to their inherent instability. Emulsion formulations include water-in-oil and oil-in-water emulsions, multiple water/oil/water emulsions, microemulsions, microdroplets, and liposomes.

A microemulsion is a transparent or substantially transparent emulsion which is formed spontaneously or substantially spontaneously when its components are brought into contact. Microemulsions are thermodynamically stable and contain dispersed particles or droplets of a diameter less than about 200 nm, more preferably less than about 150 nm. These particles may be spherical, although other structures are possible, such as liquid crystals with lamellar, hexagonal or isotropic symmetries.

Microemulsions can also be used as a "microemulsion preconcentrate", defined herein as a composition which spontaneously forms a microemulsion in an aqueous medium, for example in water, upon dilution, or in the gastric juices after oral application. The microemulsion can be diluted in water at a ratio of about 1:1 to about 1:10 by volume.

While emulsion-based delivery systems are useful for certain applications, the delivery vesicles are subject to physical rupture because of the delicate nature of the liquid/membrane/liquid structure. Emulsion based delivery systems also have relatively short release times. Further, it is difficult to isolate emulsion based vesicles from the aqueous media used for storage for subsequent reconstitution.

In spite of these difficulties, microemulsions have been used as successful delivery systems for certain types of pharmaceutical compounds, particularly compounds such as members of the cyclosporin class, which are cyclic oligopeptides. This carrier generally contains a hydrophilic solvent, such as liquid polyethylene glycol (PEG) 200-600, ethylene or propylene glycol, ethanol or propanol, glycerin, water, soluble fatty acid C6-C18 esters of sucrose, dimethylisosorbide, ethyl-acetate, glycofurol (fatty acid derivative of a cyclic polyol), PEG derivatives of tocopherol, or PEG-fatty acid esters; and a surfactant, such as TWEEN™ 20 (ICI Americas, Inc.) which is polyoxyethylene sorbitan monolaureate. Other ingredients include various PEG (polyethylene glycol) derivatives or phospholipids; a water-insoluble oil such as corn oil, other oils from plants and mixtures of oils; and CREMOPHOR® (BASF Corp.), which is ethoxylated castor oil and similar PEG derivatives of castor oil or other fats which are used as an amphiphilic solvent, emulsifier, surfactant, etc.

The microemulsions described above are typically droplets of oily material dispersed in water. Liquid droplets have limited stability and may rupture in response to changes in pH, ionic strength, or temperature.

It is therefore an object of then invention to provide microemulsions with increased stability.

It is another object of the invention to provide methods for the preparation of microemulsions with increased stability.

It is yet another object of the invention to provide methods of using microemulsions with increased stability in medical and non-medical applications.

BRIEF SUMMARY OF THE INVENTION

A formulation containing one or more lipophilic agents, methods of making and using the formulation are described herein. The formulation is formed by adding a pre-suspension concentrate composition to an aqueous medium. Upon contact with the aqueous medium, a solid nanoparticle suspension spontaneously forms. The resulting formulation is in the form of a microemulsion. The concentrate contains an amphiphilic solvent, a pharmaceutically acceptable solid carrier such as a solid fatty acid or ester, a surfactant, and an agent. Preferably the concentrate contains a combination of a surfactant with a high hydrophilic/lipophilic balance (HLB) of at least about 8 and a surfactant with a low HLB of less than about 5. The agent is preferably a lipophilic drug and other lipophilic ingredient, such as vitamins. The composition is suitable for use in medical and non-medical applications. The microemuslions described herein have increased stability was compared to the prior art.

DETAILED DESCRIPTION OF THE INVENTION

I. Definitions

As used herein, "concentrate" or "pre-suspension concentrate" generally refers to a composition which spontaneously forms a nanoparticulate dispersion (also referred to herein as "microemulsion") in an aqueous medium, for example in water upon dilution, or in the gastric juices after oral administration. The term "pre-suspension concentrate" includes those compositions that form solid particles having a mean diameter of less than about 500 nm upon contact with an aqueous medium. Dilution of the pre-suspension concentrate in water can be for example from about 1:1 fold to about 1:1000 by volume.

As generally used herein, "solid component" includes solid materials that are solid at room temperature (defined herein as 25°C.) and that dissolve in the "pre-suspension concentrate" composition, which upon dispersion in aqueous medium becomes part of the formed solid nanoparticles. Examples of solid components include fatty acids and fatty alcohols and their esters that melt at temperatures above 25°C.; solid polymers; waxes and fats.

As used herein, "solid fat" generally refers to pharmaceutically acceptable carriers which are solid at room temperature as defined above.

As used herein, "lipophilic agents" generally refers to active agents which are slightly soluble in water and which can be delivered in nanoparticles, particularly those active agents having pharmaceutical efficacy.

II. Composition

A formulation for the administration of lipophilic agents with high bioavailability has been developed. This formulation includes an amphiphilic solvent which is preferably a lower alkyl ester of lactic acid, a pharmaceutically acceptable solid carrier such as solid fatty acids and esters, and a surfactant, preferably a combination of a surfactant with a high HLB of at least about 8 and a surfactant with a low HLB of less than about 5. The hydrophilic solvent is preferably ethyl lactate, propyl lactate, isopropyl lactate, butyl lactate, hexyl lactate, isohexyl lactate, or a mixture thereof. All components are soluble in the amphiphilic solvent to form a homogeneous clear solution.

Other ingredients are optional, including but not limited to, a phospholipid, an ethoxylated fat such as CREMOPHOR® or another similar substance, cationic or anionic lipids such as long chain fatty acids or amines and phospholipidic acids or amines, or a mucoadhesive polymer or a lipid-polyethylene glycol conjugate that will form nanoparticles with surface charged, mucoadhesive, or hydrophilic properties. Optionally, a sufficient amount of the ethoxylated fat such as CREMOPHOR® is substituted for the surfactant.

The preferred particle size in the resultant formulation is preferably less than about 500 nm, more preferably less than about 100 nm, and most preferably from about 5 nm to about 50 nm. In fact, as described in greater detail below, the resultant formulation preferably includes particles sized less than about 100 nm in order to be suitable for the administration of lipophilic agents with effective bioavailability in humans.

The formulations are stable. The formulations have the advantage of not requiring stabilizers, such as antioxidants, for good stability. The excellent stability and the ability to spontaneously form a nanoparticulate suspension are believed to be both due to the use of a combination of amphiphilic solvents such as ethyl lactate and a solid carrier.

a. Amphiphilic Solvent

The amphiphilic solvent is preferably selected from the family of lower alkyl esters of lactic acid or alternatively from the family of lower alkyl lactone esters or N-methylpyrrolidone. Hereinafter, the term "lower alkyl" includes C1 to C8, for example methyl, ethyl, propyl, isopropyl and hexyl esters. More preferably, the amphiphilic solvent is methyl lactate, ethyl lactate, propyl lactate, spironolactone or N-methylpyrrolidone.

N-methylpyrrolidone (NMP) is a powerful amphiphilic solvent that dissolves both hydrophilic and hydrophobic compounds such as paclitaxel, steroids, peptides, proteins, saccharides and many polymers including poly(alkyl hydroxyl acids) and PEG derivatives at high concentrations. NMP is miscible with most hydrophilic and hydrophobic solvents including hexanes, ethers, ketones, lipids, alcohols and aqueous solutions. NMP is approved for use in pharmaceutical compositions including injectable formulations. A solution of poly(lactic acid) in NMP and leuprolide is in clinical use for treating prostate cancer.

Ethyl lactate (2-hydroxypropanoic acid ethyl ester) is a colorless liquid which is miscible with water, alcohol and ether. Ethyl lactate is considered to be suitable for human administration with an LD50 which was higher than 5 g/kg in mice when given an oral dose. N-methylpyrrolidone is a colorless liquid which is miscible with water and organic solvents, and is also considered to be safe for human administration. N-methylpyrrolidone is used in the clinic as a solvent for a polymeric in situ implant to treat gingivitis.

Ethyl lactates, and other members of this family of amphiphilic solvents such as propyl lactate, isopropyl lactate, butyl lactate, hexyl lactate and isohexyl lactate, have unexpectedly good properties for the described formulations. For example, ethyl lactate is miscible in both organic and inorganic solvents, since it is more hydrophobic than ethanol. Ethyl lactate is less volatile than ethanol and thus has higher storage stability than ethanol. The properties of the molecule are related to its molecular structure, which features an alcohol group or radical, and an ester group or radical. Without wishing to be limited by a single hypothesis, the dominant functionality of this molecule is related to the alcohol group, which allows the formation of hydrogen bonds, and thus provides hydrophilicity to the molecule. The alcohol group also contains a hydrophobic part, through the carbonyl group of the ester bond, which allows the formation of hydrogen bonds with alcohols. This molecule has the ability to form internal and external hydrogen bonds. The solubilization of the various lipophilic agents to be formulated in the invented formulation can be adjusted by selecting the proper alkyl ester of lactic acid, as the use of longer alkyl residues results in a higher degree of solubilization of the lipophilic agent. The diffusion of alkyl lactates to the water phase is much slower than ethanol, and the diffusion into water from a water free formulation is slower as the alkyl chain of the lactate ester is longer.

In a preferred embodiment, a combination of a solvent selected from the family of lower alkyl esters of lactic acid and a solvent selected from the family of alkyl lactone esters or N-methylpyrrolidone is employed, rather than a single solvent as described above. Optionally, any of these solvents can be combined with other hydrophilic organic solvents such as ethylene glycol, glycofurol or PEG 400.

b. Surfactant

A suitable surfactant is preferably a combination of a surfactant with a high HLB (hydrophilic/lipophilic balance) of at least about 8 and a surfactant with a low HLB of less than about 5. The term "HLB" refers to the hydrophilic/lipophilic balance of a surfactant. A surfactant with high HLB is hydrophilic, while a surfactant with low HLB is hydrophobic. Therefore, the combination of a surfactant with high HLB and a surfactant with low HLB, is actually a combination of a hydrophilic surfactant and a hydrophobic surfactant.

Particularly preferred combinations of these surfactants feature a large difference between the HLB of the low HLB surfactant and that of the high HLB surfactant. Therefore, one example of such a particularly preferred combination is a combination of TWEEN™ 20 and SPAN™ 80 which is sorbitan monolaurate, although other such combinations could be also be used. SPAN™ hydrophobic surfactants are a group of sorbitan fatty acid esters such as sorbitan monooleate, sorbitan monopalmitate, sorbitan monostearate, sorbitan tristearate, sorbitan monooleate, sorbitan trioleate and sorbitan monolaurate. SPAN 80 is an example of a low HLB surfactant, with an HLB of 4.3, and is sorbitan monooleate. SPAN hydrophobic surfactants are commercially available from various producers, including Capital City Products, Croda Chem, ICI, Lippo Chem. and Atlas, under various commercial names: ARLACEL™, Armotan, Crill, EMSORB™, LIPOSORB™, Protachem, and Sorbester.

Illustrative, non-limiting examples of suitable surfactants from this group, with HLB values given in parentheses, are as follows: SPAN™ 60 (4.7) SPAN™ 65 (2.1). SPAN™ 80 (4.3), SPAN™ 85 (1.8), ARLACEL™ 83 (3.7), ARLACEL™ ITM C (1.7), ARLACEL™ 85 (1.8), ARLACEL™ 80 (4.3), and ARLACEL™ 60 (4.7). These molecules are generally soluble in oil. They are also soluble in most organic solvents. In water they are generally insoluble but dispersible. Other low HLB surfactants include but are not limited to PEG-6 glyceryl monooleate (HLB of about 3 or 4), and propylene glycol laurate (HLB of 4).

TWEEN hydrophilic surfactants (polysorbates) are a family of PEG sorbitan esters (polyoxyethylene-sorbitan-fatty acid esters), for example mono- and tri-lauryl, palmityl, stearyl and oleyl esters of the type known and commercially available under the trade name TWEEN. TWEEN® 20 (polyoxyethylene (20) sorbitan monolaurate) has an HLB of 16.7. Other types of TWEEN® (ICI Americas Inc.) surfactants may also be useful for the compositions disclosed herein.

TWEEN® surfactants are soluble in water but not in oil. The chemical structure of this family of surfactants features one, two or three short PEG chains, generally of about 5 to 20 ethylene glycol units, connected by an ester bond to sorbitan. These surfactants are produced by various companies (Croda, ICI, Sandoz, Mazer, Atlas) and may appear under various trade names, besides TWEEN: SORLATE™, MONITAN™, CRILLET™ and so forth. Members of this family which are polysorbates 20, 21, 0, 60, 61, 65, 80 and 85 have an HLB be TWEEN 11 and 16.7, and therefore would optionally be suitable as high HLB surfactants.

Other suitable high HLB surfactants may be obtained from manufacturers such as Gattefosse Ltd., and include but are not limited to, sucrose fatty acid esters such as saccharose monopalmitate (HLB of 15) and saccharose monostearate (HLB of 11) or PEG-32 glyceryl laurate (HLB of 14). Suitable high HLB nonionic surfactants include but are not limited to polyethylene glycol (PEG) nalkanol esters of the Brij family such as Brij and 99 which have an HLB in the range of 12.4 to 16.9. Brij 56 is polyoxyethylene [10] cetyl ether and is an example of such a high HLB surfactant which can be substituted for TWEEN 20 or CREMOPHOR. Brij 56 has an HLB of 12.9.

c. Phospholipid

In an alternative embodiment, a phospholipid is incorporated into the formulation. A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lecithins are available with acyl chain lengths ranging from 4 to 19 carbons. The preferred lecithins for biological applications are those with alkyl chain lengths in the biological range (10 to 18 carbons). Naturally occurring lecithin can be obtained from a variety of sources such as egg, bovine heart, or soy bean. Unsaturated lecithins (dioleoyl; dilinoleoyl; alpha-palmitoyl, beta oleoyl; alpha palmitoyl, beta linoleoyl; and alpha oleoyl, beta palmitoyl), dianachidonyl lecithin (highly unsaturated and a prostaglandin precursor), and alpha palmitoyl beta myristoyl lecithin are also available. Certain phospholipids, such as phosphatidic acid, phosphatidyl serine, phosphatidyl inositol, cardiolipin (diphosphatidyl glycerol), and phosphatidyl glycerol, can react with calcium in serum, causing aggregation or the binding of liposphores to cell membranes.

These unfavorable reactions can be minimized by combining these phospholipids with non calcium-binding phospholipids such as phosphatidylcholine. Phosphatidic acid can be isolated from egg or prepared synthetically (dimyristoyl, dipalmitoyl and distearoyl derivatives are available from Calbiochem). Bovine phosphatidyl serine is also available commercially (Sigma Chemical Co. St. Louis, Mo.). Phosphatidyl inositol can be isolated from plant or bovine sources. Cardiolipin can be purified from bovine or bacterial sources. Phosphatidyl glycerol can also be purified from bacteria. All are commercially available.

d. Pharmaceutically Acceptable Solid Carrier

In a preferred embodiment, the formulation includes a pharmaceutically acceptable solid carrier which can be a fatty acid ester, fatty acid, fatty alcohol or fatty amine, or a polymer. One non-limiting example of a fatty acid ester is tricaprin. Tricaprin is a hydrophobic triester of glycerol and caproic acid. Tricaprin does not dissolve in water and thus remains as a component of the dispersed lipophilic drug-loaded particles after dispersion in aqueous solution. Tricaprin solubilizes many lipophilic agents in a fatty medium which is dispersed by the hydrophilic-hydrophobic dispersing agents. Other such fatty components which are suitable as replacements for tricaprin include, but are not limited to, pure and mixed alkyl esters of fatty acids and mixtures thereof. Examples include ethyl esters of fatty acids such as ethylstearate and ethylpalmitate; and triglycerides such as trilaurin and trimyristin. Mixtures of fats include hydrogenated vegetable oils. The preferred fats are those that solubilize lipophilic agents with a melting point above 25°C., such that the resultant pre-suspension concentrate formulation forms a nanodispersion of solid particles. Wax compositions of long chain fatty acid esters of long chain alcohols are also suitable. Biopolymers such as polycaprolactone, polylactide, poly (lactide-glycolide), and poly(hydroxy butirate) can be used as solid carrier to form the nano-suspension. The solid carrier can be formed in situ when the oily composition is mixed in an aqueous medium either by chemical reaction induced by reagents in the pre-suspension oily composition or in the aqueous phase or by reacting with the aqueous phase.

Suitable mucoadhesive ingredients that may be added to the pre-suspension concentrate liquid formulation, in order to form nanoparticles with mucoadhesive surface properties include, but are not limited to, hydroxypropyl cellulose derivatives, poly(vinyl alcohol) derivatives, alginates, hyaluronan, and other molecules that have specific adhesive properties to mucosal tissue.

e. Agents to be Delivered

The agent in the formulation is a lipophilic compound. Lipophilic compounds, as defined herein, are compounds, which are substantially insoluble in water at 25°C. and are non-proteinous substances.

i. Biologically Active Agents

Suitable lipophilic compounds include biologically active agents which act locally in the mouth or systemically, which in the case of the latter, can be administered orally, to transmit the active component into the gastrointestinal tract and into the blood, fluids, and tissues of the body. Representative lipophilic drugs include antacids, anti-inflammatory substances, coronary vasodilators, cerebral vasodilators, psychotropics, antineoplastics, stimulants, anti-histamines, laxatives, decongestants, vitamins, gastrointestinals, anti-diarrheal preparations, antianginal drugs, vasodilators, anti-arrythmics, anti-hypertensive drugs, vasoconstrictors, antimigraine drugs, anti-coagulants and anti-thrombotic drugs, analgesics, anti-pyretics, hypnotics, sedatives, anti-emetics, anti-nauseants, anticonvulsants, anti-epileptics, neuromuscular drugs, drugs acting on CNS (Central Nervous System), linear peptides, proteins, hyper- and hypoglycemic agents, thyroid and anti-thyroid preparations, diuretics, anti-spasmodics, uterine relaxants, mineral and nutritional additives, anti-obesity drugs, anabolic drugs, anti-asthmatics, expectorants, cough suppressants, mucolytics, anti-uricemic drugs, and other drugs or substances acting locally in the mouth, such as topical analgesics, local anaesthetics, and combinations thereof.

For non-medical applications, suitable active agents include dyes, colorants, stabilizing agents, antioxidants, plant extract, essential oils, pesticides, sunscreens, herbicides, fertilizers, perfumes, and vaccines.

ii. Industrial Applications

Pre-suspension concentrates that spontaneously form solid nanoparticle suspension upon contact with aqueous fluids may contain suitable lipophilic agents for use in industrial applications such as oils, electronics, thin-layer coatings, heterogenic catalysis, lithography and the like.

III. Method of Making the Composition a. Pre-Suspension Concentrate

A pre-suspension concentrate is prepared by dissolving the lipophilic agent in a water-miscible organic solvent to form a mixture. Optionally, the solvent is approved for oral use. The phospholipid is dissolved in this mixture, with gentle heating and mixing. The surfactant and solid material are added and dissolved in the mixture to form an oily, transparent and homogeneous solution. The pre-suspension concentrate has a small volume. When the pre-suspension concentrate is added to aqueous solution, it is spontaneously dispersed to form a dispersion.

b. Nanoparticles

A liquid oily pre-suspension concentrate of a reactive monomer or oligomer may be added to an aqueous solution to spontaneously form a nanodispersion. Optionally, the pre-suspension concentrate features one or more catalysts or curing agents that solidify the nanodispersion to a nanosuspension upon interaction with the aqueous medium. For example, a clear solution of lauryl methacrylate, benzoyl peroxide, TWEEN™ 80, SPAN™ 20, and ethyl lactate are added with mixing to hot water (e.g., above room temperature, for example 70°C.). The oily solution is spontaneously dispersed into a nanodispersion where the nanodispersion is converted to solid nanoparticles as a result of radical polymerization initiated by the contact with the hot water. Alternatively, polymerization of the nanodispersion can be initiated at room temperature where the radical source is water soluble and thus polymerize the monomers in the dispersed organic solution.

Other methods of initiation of radical polymerization are well known in the art. For example, the radical source for polymerization is dissolved in the aqueous solution, i.e. redox based catalysts such as ammonium persulfate, and hydrogen peroxide/$FeCl_3$ mixture, and thus upon contact with the aqueous solution polymerization occurs by the radicals in the water solution, causing a phase change to form nanoparticles.

In other cases, a phase change may take place to in situ formation of nanoparticulate suspension due to interaction with water, pH, ionic strength, or temperature change. For example, ricinoleic acid based polyanhydrides and polyesters that are liquid at room temperature and above that upon addition to aqueous medium solidify to solid or semi solid mass due to interaction with water. Another example is a copolymer of polyethylene glycol (PEG) and polylactic acid (PLA) that are liquid at room temperature but solidify at temperatures above 30°C. Mixing pre-suspension solutions containing these phase change PEG-PLA with aqueous medium at 30°C. or above causes a nanosuspension to be formed in water.

Polymerizable pre-suspension concentrated mixtures can be used for the preparation of molecularly imprinted nanoparticles. Molecular imprinting is a method where an imprinted molecule is dissolved within a solution mixture of various vinyl monomers and divinyl monomers where upon polymerization a network rigid polymer matrix is formed around the imprinted molecule. Extraction out of the imprinted molecule results in cavities of a reciprocal topology to the imprinted molecule.

The process described above for polymerization of nanodroplets to form solid polymers is well suited for the preparation of imprinted nanoparticles in a single step. For example, a mixture of estradiol (10%), acrylic acid (20%), ethyleneglycole dimethacrylate (70%) is mixed with the proper amount and type of surfactant and a water miscible organic solvent that contain benzoyl peroxide (0.5% per monomers) as initiator. Upon addition to hot water (60°C.) radical polymerization takes place which result in nanoparticles with imprinted estradiol. The estradiol is extracted out by ethanol to form an imprinted polymeric nanoparticles for estradiol. The particles will recognize preferentially estradiol from a mixture of cholesterol derivatives. Alternatively, the acryl ester of estradiol is added instead of estradiol, which results in particles with estradiol bound within the polymer matrix. Estradiol residue is released from the polymer matrix by exhaustive hydrolysis in alcoholic solution of sodium hydroxide or piperidine. The imprinted polymer using this method is more specific than the imprinted particles prepared with free estradiol.

Preparation of cyanoacrylate nanoparticles and nanocapsules: cyanoacrylate monomers such as ethyl, butyl, or iso-octyl cyanoacrylate are mixed in a solution of surfactants and a water soluble organic solvent. The solution is acidified with acetic acid or any acid so that the cyanoacrylate is not spontaneously polymerized. The pre-suspension concentrate having cyanoacrylate is dispersed in aqueous medium with shaking. Capsules loaded with active agents added to the solution prior to addition to water are obtained.

The morphology and structure of lipid particles was studied using Transmission Electron Microscopy (TEM). Analysis of the particle size distribution of the lipospheres was performed using N4 Coulter Counter Particle Size Analyzer, or ALV-NIBS/HPPS, high performance particle sizer.

The oily formulations which, upon contact with aqueous media, spontaneously form a nanosuspension, were loaded in a controlled delivery system so that the oil was exposed to the aqueous media gradually for an extended time period, thereby providing a longer time period for nanosuspension formation and for active agent exposure. The oily formulations are loaded in an osmotic minipump or capsule. The pump pushes the oil out of the capsule, which then spontaneously forms the nanosuspension upon exposure to the outside aqueous media. A nanosuspension is formed as long as the oily presuspension concentrate is released from the device. The release can be also by passive diffusion of the oil from a capsule having creaks or holes at the time it is immersed in aqueous medium. Another possibility is to absorb the oily formulation in a porous polymeric or inorganic matrix that allows the diffusion of the oil to the surface to form the nanosuspension.

In a typical experiment, the pre-suspension concentrate of any of the formulations described in the examples is loaded in a flexible envelop having an orifice or orifices which is then packed in a second envelop or capsule that at least part of it is made of a semi-permeable membrane such as cellulose dialysis tubing with a 12,000 molecular weight cut off. In between the two envelopes, a water soluble salt such as sodium or calcium chloride. When this system is placed in an aqueous media, water is penetrating through the semi-permeable membrane dissolving the salt which result in an osmotic pressure that push the pre-suspension oil out to the aqueous medium through the orifice or orifices. Alternatively, the pre-suspension concentrate oil is loaded in an envelope or capsule that at least part of it is made of a semi-permeable membrane having an orifice or orifices. To this envelop, a fine powder of sodium or calcium chloride at an amount that will create enough osmotic pressure inside the envelope that will push out the oil or the partially dispersed oil through the orifice.

Controlled release can be obtained when the solid core is a polymer or hydrophobic lipid. For example, a solution of polylactide, a peptide or protein such as an enzyme or vaccine, surfactants and NMP as organic water miscible solvent prepared. Upon addition of the solution to water, nanoparticles entrapping the protein are obtained which release the protein upon degradation of the polymer.

The formulations can be administered by injection, in a capsule, or by other standard methods.

For non-medical applications, including agricultural applications, mechanical means of gradual exposure of the oily formulation to an aqueous medium, such as spraying or dripping, can be used to form the microemulsion.

The methods and compositions described above will be further understood with reference to the following non-limiting examples.

EXAMPLES

Materials: Methyl Lactate, Ethyl lactate, Propyl Lactate, Isopropyl Lactate, Butyl Lactate and 2-Ethylhexyl Lactate were obtained from Purac biochem, The Netherlands. Trilaurin was obtained from Lipo Chemicals inc., Paterson, N.J. Tricaprin was obtained from Sasol, Germany GmbH. TWEEN 80 and SPAN 20 were obtained from Sigma chemical Co., St. Louis, Mo. L-Phosphatidylcholine 95% was obtained from Avanti Polar lipids, inc. Alabaster, Ala.

In these non-limiting examples, formulations of Ceftriaxone, Pravastatin Lactone, Paclitaxel or Bupivacaine free base (5% w/w) together with tricaprin or trilaurin, phospholipid (L-α-phosphatidylcholine, 95%, egg) and TWEEN™ 80, SPAN™ 20 and/or ethoxylated castor oil were dissolved in lactate esters.

Example 1

Particle Size of Ceftriaxone Pre-Suspension Concentrate Formulations

Tables 1-4 summarize the particle size (radius) of Ceftriaxone formulations prepared by the pre-concentrate method. The influence of each component, and the effect of changing the amount and/or replacing the component, was examined.

The difference in particle size of the formulation with and without an emulsifier, TWEEN™ 80, is shown in Table 1. The particle size is smaller when TWEEN™ 80 is incorporated into the formulation.

The effect of using TWEEN™ 80, SPAN 80, or a mixture of the two on the particle size is shown in Table 2. The use of TWEEN™ 80 alone results in a smaller particle size.

The effect of emulsifier concentration on particle size is shown in Table 3. Increasing the concentration of TWEEN™ 80 does not significantly affect the particle size.

The effect of fatty component concentration on particle size is shown in Table 4. Decreasing the concentration of the fatty component decreases the particle size.

The effect of the presence of CREMOPHOR® on the particle size of the formulation is shown in Table 5.

TABLE 1

Ceftriaxone Pre-concentrate Formulations Using TWEEN ™ 80 as an Emulsifier

|  | A-1 | A-2 | A-4 | A-21-1 |
|---|---|---|---|---|
| Ceftriaxone (mg) | 2.5 | 2.5 | 2.5 | 2.5 |
| Tricaprin (mg) | 5 | — | — | — |
| Trilaurin (mg) | — | 5 | 5 | 5 |
| PL egg (mg) | 2.5 | 2.5 | 2.5 | 2.5 |
| TWEEN ™ 80 (mg) | — | — | 4 | 10 |
| SPAN ™ 80 (mg) | — | — | — | — |
| Ethyl lactate (mg) | 40 | 40 | 33 | 31 |
| Mean Particle size after dispersion (nm) | 210 | 175 | 72 | 70 |

TABLE 2

The Effect of Emulsifiers on Ceftriaxone Pre-suspension Concentrate Formulations

|  | B-21-2 | B-21-3 | B-1-21-4 |
|---|---|---|---|
| Ceftriaxone (mg) | 2.5 | 2.5 | 2.5 |
| Trilaurin (mg) | 10 | 5 | 5 |
| PL egg (mg) | 2.5 | 2.5 | 2.5 |
| TWEEN ™ 80 (mg) | 10 | — | 5 |
| SPAN ™ 80 (mg) | — | 10 | 5 |
| Ethyl lactate (mg) | 27 | 29 | 28 |
| Mean Particle size after dispersion (nm) | 94 | 155 n | 177 |

TABLE 3

The Effect of Emulsifier Concentration on Particle Size of Ceftriaxone Concentrate Formulations

|  | E-98-1 | E-98-2 |
|---|---|---|
| Ceftriaxone (mg) | 5 | 5 |
| Trilaurin (mg) | 10 | — |
| Tricaprin (mg) | — | 10 |
| PL egg (mg) | 5 | 5 |
| TWEEN ™ 80 (mg) | 40 | 40 |
| SPAN ™ 80 (mg) | — | — |
| Ethyl lactate (mg) | 40 | 40 |
| Mean Particle size after dispersion (nm) | 80 | 68 |

TABLE 4

The Effect of Concentration of the Fatty Component on Particle Size of Ceftriaxone Pre-suspensionCconcentrate Formulations

|  | E-99-1 | A-99-2 | A-99-3 |
|---|---|---|---|
| Ceftriaxone (mg) | 2.5 | 2.5 | 2.5 |
| Trilaurin (mg) | 2.5 | 5 | 2.5 |
| PL egg (mg) | 2.5 | 2.5 | 1 |
| TWEEN ™ 80 (mg) | 20 | 20 | 20 |
| SPAN ™ 80 (mg) | — | — | — |
| Ethyl lactate (mg) | 20 | 20 | 20 |
| Mean Particle size after dispersion (nm) | 48 | 63 | 57 |

TABLE 5

The Effect CREMOPHOR ® on the Particle Size of Ceftriaxone Pre-concentrate Formulations

|  | A-101-4 | A-101-5 | A-101-6 | A-101-7 |
|---|---|---|---|---|
| Ceftriaxone (mg) | 20.4 | 20.1 | 20.8 | 20.6 |
|  | 5.3% w/w | 5.5% w/w | 5.4% w/w | 5% w/w |
| Trilaurin (mg) | 21.9 | 20.9 | 19.9 | 20.2 |
| PL egg (mg) | 20.2 | 22.1 | 20.2 | 20.9 |
| TWEEN ™ 80 (mg) | 160.1 | 80.6 | — | 51 |
| Ethoxylated Castor oil (mg) | — | 63.4 | 158 | 177 |
| Ethyl lactate (mg) | 164 | 160.4 | 166 | 120 |
| Mean Particle size After dispersion (nm) | 54.1 | 83 | 116 | 50.8 |

Example 2

Pravastatin Lactone Pre-Concentrate Formulation

Pravastatin Lactone formulations prepared by the pre-concentrate method. The results are shown in Table 6. Formulations ER-102-1 and ER-102-2 have the smallest particle sizes obtained.

TABLE 6

Pravastatin Lactone Pre-concentrate Formulation

|  | E-102-1 | E-102-2 | E-102-3 | E-102-4 |
|---|---|---|---|---|
| Pravastatin Lactone | 21.3 | 20.7 | 21.3 | 21.3 |
| Trilaurin (mg) | 20.3 | 20.2 | 22.7 | 20.8 |
| PL egg (mg) | 21.3 | 20.6 | 22 | 21.7 |
| TWEEN ™ 80 (mg) | 165 | 86 | — | 45 |
| CREMOPHOR ® RH40 | — | 75 | 157 | 194 |
| Ethyl lactate (mg) | 164 | 159 | 155 | 99 |
| Particle size after dispersion | Mean 11.9 nm | Mean 17.1 nm | Mean 20.7 nm | Mean 85.5 nm |

Example 7

Paclitaxel Pre-Suspension Concentrate Formulations

Preparation:

Paclitaxel, ethyl stearate, TWEEN 80, and soybean phospholipid (centrolex F), or CREMOPHOR RH40 were dissolved in a minimum volume of N— methyl pyrrolidone to form a clear solution. Ethyl lactate, a water miscible organic solvent, was added to this solution. When this clear oil was added to water, it formed a nanodispersion of about 30 nanometer. The following table provides the composition of the two successful formulations. The concentration of 10 mg/ml of Paclitaxel can be increased to 40 mg/ml without affecting the particle size.

TABLE 7

Paclitaxel formulations

|  | BS-1-c | BS-1-d |
|---|---|---|
| Paclitaxel | 1 mg | 1 mg |
| Ethyl stearate | 5 mg | 5 mg |
| TWEEN ™ 80 | 16.86 mg | 18.42 mg |
| PL-(centrolex -F) | 1 mg |  |
| Polyoxyl-40 hydro Castor oil |  | 1 mg |
| Ethyl Lactate | 80 µl | 80 µl |
| NMP | 20 µl | 20 µl |
| Mean Particle Radius, nm | 20.4 | 30 |

Example 3

Stability of Pre-Suspension Concentrate Formulations

Selected pre-suspension concentrate formulations were incubated at 37°C. for 46 days in glass vials with sealed plug for stability studies. The surface morphology of liposheres before and after incubation was studied by Transmission Electron Microscopy. The particle size before and after incubation was determined by a ALV-NIBS/HPPS, high performance particle sizer.

As shown in Tables 8-10, the particle size and the external surface of the examined formulations did not change significantly for at least 46 days.

TABLE 8

Stability of Ceftriaxone Pre-concentrate Formulations

|  | ER-AV-104-1 (101-4) | 104-2 (101-7) |
|---|---|---|
| Ceftriaxone (mg) | 20 | 21.2 |
| Trilaurin (mg) | 21.8 | 20.7 |
| PL egg (mg) | 21.2 | 21.1 |
| TWEEN ™ 80 (mg) | 167 | 58 |
| CREMOPHOR ® RH40 (mg) | — | 171 |
| Ethyl lactate (mg) | 159 | 133 |
| Particle size after dispersion t = 0 | Mean 73.5 nm | Mean 53 nm |
| Particle size after dispersion t = 46 days in 37° C. degree. | Mean 10.5 nm | Mean 11.5 nm |

TABLE 9

Stability of Pravastatin Lactone Concentrate Formulations-

|  | 104-3 (102-1) | 104-4 (102-2) | 104-5 (102-3) |
|---|---|---|---|
| Pravastatin Lactone | 21.9 | 21.8 | 21.5 |
| Trilaurin (mg) | 21.9 | 20.7 | 21.9 |
| PL egg (mg) | 21.7 | 21.1 | 22.3 |
| TWEEN ™ 80 (mg) | 168 | 89 | — |
| CREMOPHOR ® RH40 (mg) | — | 104 | 155 |
| Ethyl lactate (mg) | 168 | 173 | 161 |
| Particle size (radius) after dispersion t = 0 | Mean 9.8 nm | Mean 9 nm | Mean 8.7 nm |
| Particle size (radius) after dispersion t = 46 days in 37° C. degree. | Mean 8.7 nm | Mean 6.2 nm | Mean 7.4 nm |

TABLE 10

Stability of Paclitaxel Concentrate Formulations

|  | ER-AV-104-6 (103-1) | 104-7 (103-3) |
|---|---|---|
| Paclitaxel (mg) | 21.6 | 22.8 |
| Trilaurin (mg) | 22.3 | 21 |
| PL egg (mg) | 23.2 | 21.8 |
| TWEEN ™ 80 (mg) | 174 | — |
| CREMOPHOR ® RH40 (mg) | — | 163 |
| Ethyl lactate (mg) | 161 | 155 |
| Particle size after dispersion t = 0 | Mean 34.6 nm | Mean 38 nm |
| Particle size after dispersion t = 46 days in 37° C. degree. | Mean 17.5 nm | Mean 33.2 nm |

Example 4

Drug Formulations Using Different Lactate Esters as the Water Miscible Organic Solvents Table 11 summarizes the ceftriaxone formulations prepared using different lactate esters as the water miscible organic solvents. As shown in Table 11, no difference in particle size was obtained by using different lactate in formulation.

TABLE 11A

Ceftriaxone Pre-suspension Concentrate Formulations Using Different Lactate Esters

|  | E-110-1 | E-110-2 | E-110-3 |
|---|---|---|---|
| Ceftriaxone (mg) | 10.8 | 10.4 | 11.2 |
| Trilaurin (mg) | 11.0 | 10.4 | 11.6 |
| PL egg (mg) | 9.7 | 10.5 | 11.3 |
| TWEEN ™ 80 (mg) | 56 | 48 | 57 |
| CREMOPHOR ® RH40 (mg) | 40 | 36 | 44 |
| Ethyl lactate (mg) | 69 | — | — |
| Methyl Lactate (mg) | — | 84 | — |
| Butyl Lactate (mg) | — | — | 78 |
| Particle size After dispersion | Mean 71 nm | Mean 74 nm | Mean 64.5 nm |

TABLE 11B

Ceftriaxone Pre-suspension Concentrate Formulations Using Different Lactate Esters

|  | E-110-4 | E-110-5 | E-110-6 |
|---|---|---|---|
| Ceftriaxone (mg) | 10.3 | 11.2 | 10.6 |
| Trilaurin (mg) | 10.4 | 11.2 | 10.5 |
| PL egg (mg) | 11.2 | 10.9 | 10.4 |
| TWEEN ™ 80 (mg) | 56 | 58 | 63 |
| CREMOPHOR ® RH40 (mg) | 51 | 38 | 42 |
| Isopropyl Lactate (mg) | 74 | — | — |
| 2-Ethylhexyl Lactate (mg) | — | 69 | — |
| Propyl Lactate (mg) | — | — | 79 |
| Particle size After dispersion | Mean 83 nm | Mean 81 nm | Mean 73 nm |

Table 12 summarizes the Pravastatin Lactone formulations prepared using different lactate esters as the miscible water solvents. As shown in Table 12, no difference in particle size was obtained by using different lactate solvents in the tested formulations

TABLE 12A

Pravastatin Lactone Pre-suspension concentrate Formulations Using Different Lactate Esters

|  | E-109-1 | E-109-2 | E-109-3 |
|---|---|---|---|
| Pravastatin Lactone (mg) | 10.6 | 11.8 | 10.0 |
| Trilaurin (mg) | 10.9 | 10.4 | 10.1 |
| PL egg (mg) | 11.9 | 9.7 | 10.8 |
| TWEEN ™ 80 (mg) | 52 | 61 | 50 |
| CREMOPHOR ® (mg) | 44 | 42 | 41 |
| Ethyl lactate (mg) | 77 | — | — |
| Methyl Lactate (mg) | — | 84 | — |
| Butyl Lactate (mg) | — | — | 76 |
| Particle size After dispersion | Mean 6.1 nm | Mean 6 nm | Mean 6.6 nm |

TABLE 12B

Pravastatin Lactone Pre-suspension concentrate Formulations Using Different Lactate Esters

|  | E-109-4 | E-109-5 | E-109-6 |
|---|---|---|---|
| Pravastatin Lactone (mg) | 10.0 | 10.2 | 10.3 |
| Trilaurin (mg) | 10.4 | 10.4 | 10.0 |
| PL egg (mg) | 11.4 | 10.3 | 10.7 |
| TWEEN 80 (mg) | 56 | 62 | 53 |
| CREMOPHOR (mg) | 36 | 44 | 40 |
| Isopropyl Lactate (mg) | 75 | — | — |
| 2-Ethylhexyl Lactate (mg) | — | 77 | — |
| Propyl Lactate (mg) | — | — | 87 |
| Particle size After dispersion | Mean 6.2 nm | Mean 14.3 nm | Mean 6.2 nm |

Table 13 summarizes the bupivacaine (free base) formulations prepared using different lactate esters as the miscible water solvents. As shown in Table 13, no difference in particle size was obtained by using different lactate solvents in the tested formulations.

TABLE 13A

Bupivacaine (free base) Pre-suspension concentrate Formulations Using Different Lactate Esters

|  | E-108-1 | E-108-2 | E-108-3 |
|---|---|---|---|
| Bupivacaine free base (mg) | 10.4 | 10.3 | 10.1 |
| Trilaurin (mg) | 10.5 | 11.8 | 10.7 |
| PL egg (mg) | 12.4 | 12 | 11.4 |
| TWEEN ™ 80 (mg) | 54 | 57 | 63 |
| CREMOPHOR ® (mg) | 43 | 41 | 40 |
| Ethyl lactate (mg) | 90 | — | — |
| Methyl Lactate (mg) | — | 92 | — |
| Butyl Lactate (mg) | — | — | 90 |
| Particle size After dispersion | Mean 6.8 nm | Mean 5 nm | Mean 6 nm |

TABLE 13B

Bupivacaine (free base) Pre-suspension concentrate
Formulations Using Different Lactate Esters

|  | E-108-4 | E-108-5 | E-108-6 |
|---|---|---|---|
| Bupivacaine free base (mg) | 10 | 10.8 | 10.2 |
| Trilaurin (mg) | 10.4 | 11.2 | 11.5 |
| PL egg (mg) | 10.8 | 11 | 11 |
| TWEEN° 80 (mg) | 56 | 62 | 53 |
| CREMOPHOR ® (mg) | 36 | 44 | 40 |
| Isopropyl Lactate (mg) | 75 | — | — |
| 2-Ethylhexyl Lactate (mg) | — | 77 | — |
| Propyl Lactate (mg) | — | — | 87 |
| Particle size After dispersion | Mean 4.8 nm | Mean 29 nm | Mean 5.7 nm |

Example 5

Nano-Liposphere Pre-Suspension Formulations for Skin Absorption

To qualitatively measuring the stratum corneum (SC) uptake of the nanoparticulate lipospheres with and without a stearylamine cationic surface, visible lipospheres containing a hydrophobic fluorescent probe, Nile Red (400 μg dye/g liposphere formulation), were formulated. Lipospheres were prepared by dissolving Nile red an active agent such as retinol in a solution of trimyristin (55-60°C.), stearylamine, TWEEN™ 80, phospholipids, Centrolex HR, and ethyl lactate to a clear liquid. The liquid solution was mixed with water to form the nano-suspension.

The tested formulation (0.1 ml) was absorbed in bed-aid and placed directly on the application area (ventral forearm skin) and held in place for 5 min. At the end of the exposure, the corners of the treated area were marked and the skin surface was rinse off with a gentle stream of water for 2 min and dried gently with a tissue paper. The stratum corneum at the treated site then was removed by repeated adhesive tape-stripping (2 tape strips, 8×2.6 cm, 3M Book Tape 845). Strips of adhesive tape used to remove the SC post-treatment were analyzed for Nile red by fluorescence microscopy (×100). Excitation was with monochrome laser at 425 nm and emission filter was at 500-525 nm.

A significant change in the fluorescence of adhesive tapes treated with formulations loaded with retinol with and without stearyl amine was observed. No difference in the fluorescence of adhesive tapes treated with large particle size (>5 microns) formulations with and without stearyl amine was observed. The large particles were washed out from the surface. Strong fluorescence emission was observed for both with/without stearyl amine formulations loaded with an oily perfumes.

The zeta potential of formulations AV-EG2-45-1 to AV-EG2-45-8 was determined as follows: The samples were diluted with 10 mM NaCl and analyzed with Zeta Sizer 3000 (Malvern Instruments UK). The results indicated that the surface charge of the nanoparticles was reversed by stearylamine, which made the negatively charged particles become positively charged particles. Stearylamine cationic particles possess improved skin retention. The effect of stearylamine was determined by Zeta Potential surface measurements.

Those skilled in the art will recognize, or be able to ascertain using no more than routine experimentation, many equivalents to the specific embodiments of the invention described herein. Such equivalents are intended to be encompassed by the following claims.

I claim:

1. A composition for administering a lipophilic compound, the composition comprising:

(i) at least one surfactant;

(ii) at least one solid carrier which is a solid at room temperature selected from the group consisting of fatty acid esters, polymers, fatty acids, fatty alcohols, fatty amines, paraffins or waxes, partially hydrogenated vegetable oil, fully hydrogenated vegetable oil and combinations thereof;

(iii) an amphiphilic solvent; and (iv) the lipophilic compound; and wherein the at least one surfactant, the at least one solid carrier, and the lipophilic compound form particles having a size less than about 500 nm when a solution comprising the at least one surfactant, the at least one solid carrier, the amphiphilic solvent, and the lipophilic compound are added to an aqueous medium.

2. The composition of claim 1 wherein the amphiphilic solvent is selected from the group consisting of alkyl esters of lactic acid, alkyl esters of glycolic acid, and N-methyl pyrrolidine.

3. The composition of claim 2, wherein the lower alkyl lactic acid ester is ethyl lactate.

4. The composition of claim 1 wherein the solid component is a compound that solidifies in situ upon dispersion in the aqueous medium.

5. The composition of claim 1 wherein the solid component is a phase change polymer that solidifies due to a change in temperature, pH or ionic strength or interaction with water molecules.

6. The composition of claim 1 wherein the surfactant is a mixture of two surfactants wherein one surfactant is a high hydrophilic/lipophilic balance (HLB) surfactant having an HLB of at least about 8, and the second surfactant is a low HLB surfactant having an HLB of less than 5.

7. The composition of claim 1, wherein the surfactant is selected from the group consisting of polyoxyethylene (20), sorbitan monolaurate, sorbitan monooleate and combinations thereof.

8. The composition of claim 1 further comprising an ethoxylated fat selected from the group consisting of polyethyleneglycol-hydrogenated castor oil.

9. The composition of claim 1 further comprising a phospholipid selected from the group consisting of egg phospholipids, soy phospholipids, lecithin and combinations thereof.

10. The composition of claim 1 further comprising a fatty acid ester.

11. The composition of claim 1 wherein the particle size is less than about 100 nm.

12. The composition of claim 11, wherein the particle size is in a range of from about 5 nm to about 50 nm.

13. The composition of claim 1 wherein the lipophilic compound is selected from the group consisting of antacids, anti-inflammatory substances, coronary vasodilators, cerebral vasodilators, psychotropics, antineoplastics, stimulants, anti-histamines, laxatives, decongestants, vitamins, gastrointestinals, anti-diarrheal preparations, antianginal drugs, vasodilators, anti-arrythmics, anti-hypertensive drugs, vasoconstrictors, anti-migraine drugs, anti-coagulants and anti-thrombotic drugs, analgesics, anti-pyretics, hypnotics, sedatives, anti-emetics, anti-nauseants, anticonvulsants, anti-epileptics, neuromuscular drugs, drugs acting on CNS (Central Nervous System), hyper- and hypoglycemic agents, thyroid and anti-thyroid preparations, diuretics, anti-spasmodics, uterine relaxants, mineral and nutritional additives, anti-obesity drugs, anabolic drugs, anti-asthmatics, expectorants, cough suppressants, mucolytics, anti-uricemic drugs, topical analgesics, local anaesthetics, dyes, colorants, plant extract, essential oils, herbicides, fertilizers, perfumes, vaccines, linear peptides, proteins, and combinations thereof.

14. The composition of claim 13 wherein the active agent is selected from the group consisting of ceftriaxone, pravastatin lactone, paclitaxel and bupivacaine.

15. The composition of claim 1, wherein the compound is a lipophilic compound suitable for use in industrial oils, electronics, thin-layer coatings, heterogenic catalysis, or lithography.

16. A method of making an oil-in-water microemulsion composition, comprising
   (a) preparing a pre-suspension concentrate solution, wherein the presuspension concentrate solution comprises
      (i) at least one surfactant;
      (ii) at least one solid carrier which is a solid at room temperature selected from the group consisting of fatty acid esters, polymers, fatty acids, fatty alcohols, fatty amines, paraffins or waxes, partially hydrogenated vegetable oil, fully hydrogenated vegetable oil and combinations thereof;
      (iii) an amphiphilic solvent; and
      (iv) a lipophilic compound; and
   (b) adding the pre-suspension concentrate to an aqueous medium to form the microemulsion composition,
   wherein the at least one surfactant, the at least one solid carrier, and the lipophilic compound form particles having a size less than about 500 nm, when the pre-suspension concentrate solution is added to an aqueous medium.

17. A method of using an oil-in-water microemulsion composition comprising a suspension of particles of a size of less than about 500 nm in an aqueous medium, comprising administering to a patient in need thereof a pharmaceutically effective amount of the composition, wherein the composition comprises
   (i) at least one surfactant;
   (ii) at least one solid carrier which is a solid at room temperature selected from the group consisting of fatty acid esters, polymers, fatty acids, fatty alcohols, fatty amines, paraffins or waxes, partially hydrogenated vegetable oil, fully hydrogenated vegetable oil and combinations thereof;
   (iii) an amphiphilic solvent; and
   (iv) a lipophilic compound; and
   wherein the at least one surfactant, the at least one solid carrier, and the lipophilic compound form the particles when a solution comprising the at least one surfactant, the at least one solid carrier, the amphiphilic solvent, and the lipophilic compound are added to the aqueous medium.

18. The method of claim 17 wherein the mode of administration is selected from the group consisting of oral, intravenous, intramuscular, intra-tissue, subcutaneous, and topical.

* * * * *